United States Patent [19]

Pressman et al.

[11] Patent Number: 5,312,955

[45] Date of Patent: * May 17, 1994

[54] METHOD FOR MAKING AROMATIC ORGANIC CARBONATES

[75] Inventors: Eric J. Pressman, East Greenbush; Sheldon J. Shafer, Pittsfield, Mass.

[73] Assignee: General Electric Company, Schenectady, N.Y.

[*] Notice: The portion of the term of this patent subsequent to Feb. 8, 2011 has been disclaimed.

[21] Appl. No.: 929,861

[22] Filed: Aug. 17, 1992

[51] Int. Cl.$^5$ ............................................. C07C 68/04
[52] U.S. Cl. ..................... 558/260; 558/274; 558/277
[58] Field of Search .................. 558/260, 274, 277

[56] References Cited

FOREIGN PATENT DOCUMENTS 350700   7/1988   European Pat. Off. ............ 558/274

*Primary Examiner*—Mary C. Lee
*Assistant Examiner*—Jacqueline Haley
*Attorney, Agent, or Firm*—William A. Teoli; William H. Pittman

[57] ABSTRACT

A method for making aromatic organic carbonate, such as diphenyl carbonate is provided which employs a transition metal catalyst in the form of a palladium catalyst mixture. The palladium catalyst can be used in combination with an organic cocatalyst, such as a terpyridine and a cobalt cocatalyst in the form of a cobalt complex containing a pentadentate ligand. The aromatic organic carbonate is separated from the carbonylation reaction mixture as a 1:1 molar adduct of aromatic organic carbonate such as diphenyl carbonate and aromatic organic hydroxy compound, such as phenol. The transition metal catalyst has been found to be recyclable allowing for the introduction of make up aromatic organic hydroxy compound into the reactor under ambient conditions.

8 Claims, 1 Drawing Sheet

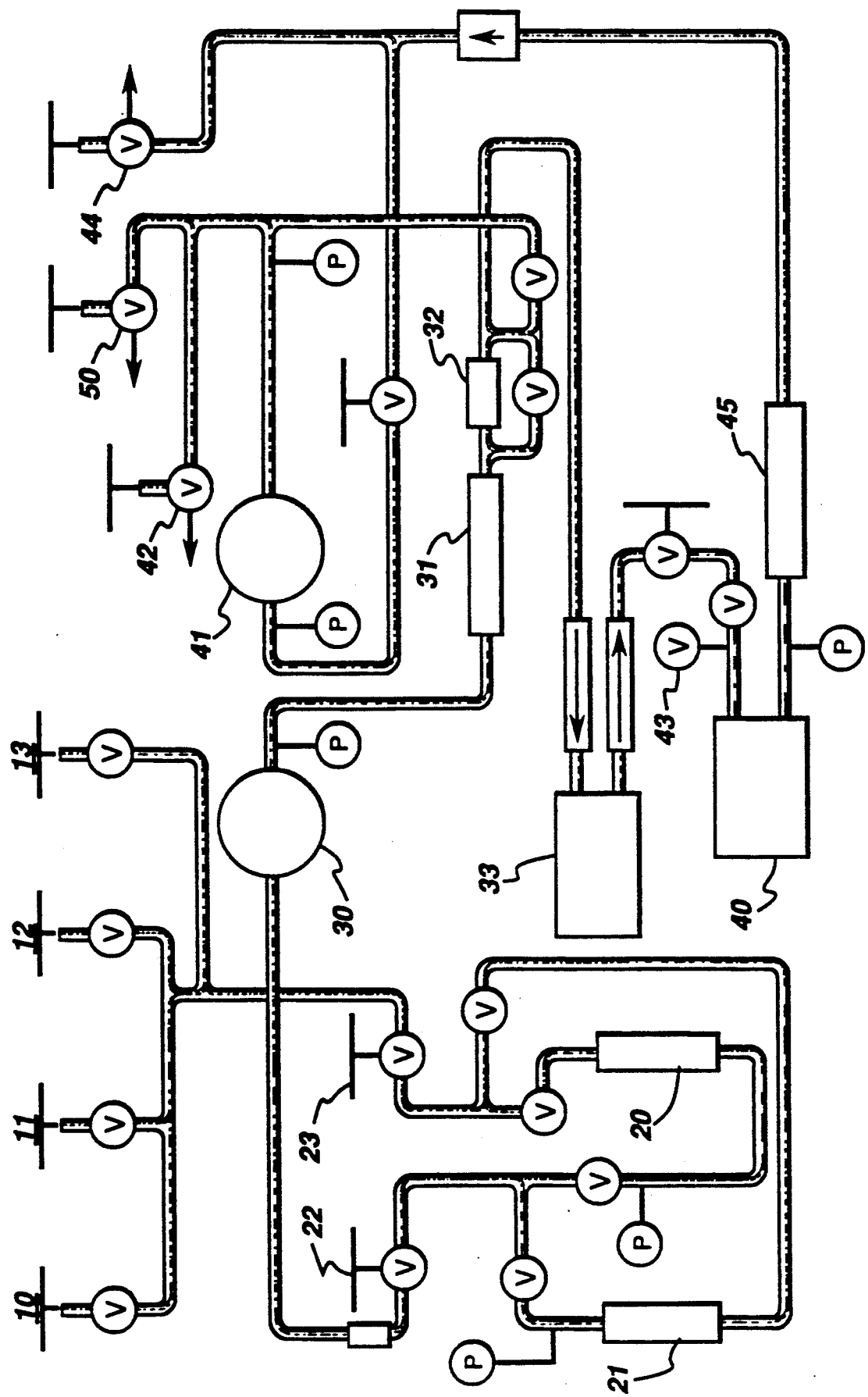

METHOD FOR MAKING AROMATIC ORGANIC CARBONATES

CROSS REFERENCE TO RELATED APPLICATION

Reference is made to copending applications 07/929,862, 07/929,749 and 07/929,860 filed concurrently herewith, and copending application serial number 07/906,681, filed Jul. 7, 1992.

BACKGROUND OF THE INVENTION

The present invention relates to a palladium catalyzed method for making aromatic organic carbonates by the direct carbonylation of an aromatic organic hydroxy compound, such as phenol. More particularly, the present invention relates to a method for making aromatic organic carbonates using recycled carbonylation catalyst present in the carbonylation reaction mother liquor after recovery therefrom of a 1:1 molar adduct of the aromatic organic carbonate and aromatic organic hydroxy compound.

Aromatic organic carbonates, such as diphenyl carbonate are of interest to thermoplastic manufacturers, since they offer an alternative non-phosgene route to aromatic organic polycarbonates by melt transesterification. A procedure for making aromatic organic carbonates using an organic solvent, such as methylene chloride, is shown by Chalk, U.S. Pat. No. 4,187,242. Additional procedures for making aromatic organic carbonates are shown by Hallgren, U.S. Pat. Nos. 4,361,519 and 4,410,464, utilizing a molecular sieve as a drying agent for the water formed during the reaction. A further procedure for making aromatic organic carbonates by catalytic carbonylation of aromatic organic hydroxy compounds is shown by Japanese patent 01,165,551. Reference also is made to EP A89111581.8, utilizing a divalent or trivalent manganese salt or cobalt (II) salt in combination with hydroquinone and a palladium catalyst to catalyze the conversion of an aromatic organic hydroxy compound to an aromatic organic carbonate.

Prior to the present invention, as shown in copending application Ser. No. 07/906,681, filed Jul. 7, 1992, some aromatic organo carbonates were made by the carbonylation of an aromatic organic hydroxy compound, such as phenol, with a mixture of carbon monoxide and oxygen which were introduced into a reactor under constant composition gas flow conditions to substantially maintain the gaseous components at a constant molar ratio and partial pressure during the course of the reaction. Although the procedure of 07/906,681 for making aromatic organic carbonates provides improved yields, the effectiveness of the transition metal catalyst, for example, the combination of a divalent or trivalent manganese salt, or cobalt (II) salt, and hydroquinone and a palladium catalyst can be substantially impaired whenever an attempt is made to introduce make-up aromatic organic hydroxy compound into the reactor under ambient conditions. It would be desirable therefore to be able to make aromatic organic carbonates, by the direct carbonylation of aromatic organic hydroxy compounds, such as phenol using constant composition gas flow conditions, by providing recyclable transition metal catalyst to allow the introduction of make-up aromatic organic hydroxy compound, such as phenol into the reactor under ambient conditions.

SUMMARY OF THE INVENTION

The present invention is based on the discovery that a mixture of a palladium catalyst and an organic amine, such as a terpyridine compound, as shown in copending application RD-21,636, or a palladium catalyst and a cobalt complex, containing a pentadentate ligand, such as a Schiff base, as shown in copending application RD-21,705, can be used in the production of aromatic organic carbonates under constant composition gas flow conditions of oxygen and carbon monoxide. After being used, the resulting transition metal catalyst has been found to retain its catalytic activity under ambient conditions for a sufficient period of time to permit the introduction of make-up organic hydroxy compound, such as phenol into the carbonylation reactor. Recovery of the aromatic organic carbonate is facilitated by the initial formation and separation of a crystalline 1:1 molar adduct of aromatic organic carbonate and aromatic hydroxy compound from the carbonylation mixture, while recyclable transition metal catalyst remains in the carbonylation reaction mixture mother liquor.

STATEMENT OF THE INVENTION

A method for making aromatic organic carbonates which comprises,
(1) charging a reactor with aromatic organic hydroxy compound and an amount of a transition metal catalyst which is sufficient to catalyze the carbonylation of the aromatic organic hydroxy compound,
(2) introducing a mixture of oxygen and carbon monoxide into the reactor and thereafter agitating and heating the resulting mixture to a temperature of about 60° C. to about 150° C., while maintaining the total reaction pressure and the partial pressures of carbon monoxide and oxygen in the mixture substantially constant until the aromatic organic hydroxy compound is substantially converted to aromatic organic carbonate,
(3) allowing the resulting mixture of (2) to cool to a temperature of from about 50° C. to about 25° C., to form a 1:1 molar adduct of aromatic organic carbonate and aromatic organic hydroxy compound,
(4) recovering the 1:1 molar aromatic adduct of (3) and,
(5) heating the 1:1 molar aromatic adduct to a temperature in the range of 40° C. to 180° C. under reduced pressure to effect the separation of aromatic organic hydroxy compound, where the transition metal catalyst is a member selected from the class consisting of,
  (a) a mixture consisting essentially
    (i) 1 gram atom, per 800–10,000 moles of aromatic organic hydroxy compound, of a palladium material selected from catalytically active palladium or chemically combined palladium,
    (ii) 0.5–5.0 gram atom, per gram atom of palladium, of metal in the form of a cocatalyst selected from divalent or trivalent cobalt or manganese or copper compounds selected from the class consisting of salts, complexes with diketones, and complexes with carbon monoxide,
    (iii) 0.1 to 2 moles, per gram atom of palladium, of an aromatic organic amine selected from terpyridines, phenanthrolines and quinolines, and (iv) 10 to 100 moles, per gram atom of palladium, of a quaternary ammonium or phosphonium halide, and (b) a mixture consisting essentially of (v) 1 gram atom, per 800–10,000 moles of aromatic organic hydroxy compound of the palladium material of (a)(i), (vi) 0.5 to 5 gram atoms of cobalt, per gram atom of palladium, of a cobalt cocatalyst comprising a cobalt complex containing a pentadentate organic ligand, and a mixture of 0 to 0.5 moles of an aromatic amine of (a)(iii), per gram atom of cobalt of such cobalt complex containing a pentadentate ligand, and (vii) 10 to 100 moles, per gram atom of palladium, of a quaternary ammonium or phosphonium halide of (a)(iv).

In a further aspect of the present invention there is provided a method for making aromatic organic carbonate which comprises, (6) adding make-up aromatic organic hydroxy compound to the mother liquor formed in step (4) of the above carbonylation reaction mixture from which a 1:1 molar adduct of aromatic organic carbonate and aromatic organic hydroxy compound has been recovered, (7) introducing a mixture of oxygen and carbon monoxide into the reactor and thereafter agitating and heating the resulting mixture to a temperature of 60° C. to 150° C., while maintaining the total reaction pressure and the partial pressures of carbon monoxide and oxygen in the mixture substantially constant until the aromatic organic hydroxy compound is substantially converted to aromatic organic carbonate, (8) allowing the resulting mixture of (7) to cool to a temperature of about 50° C. to about 25° C., to form a 1:1 molar adduct of aromatic organic carbonate and aromatic organic hydroxy compound, (9) recovering the 1:1 molar aromatic adduct of (8) and,

(10) heating the 1:1 molar aromatic adduct to a temperature in the range of 40° C. to 180° C. under reduced pressure to effect the separation of aromatic organic hydroxy compound, Aromatic organic hydroxy compounds which can be used in the practice of the present invention are for example, phenol, o-cresol, p-cresol, 2-6-xylenol, and mesitol The palladium material useful as a catalyst can be in elemental form, or it can be employed as a palladium compound. Accordingly, palladium black or elemental palladium deposited on carbon can be used as well as palladium compounds, such as halides, nitrates, carboxylates, oxides and complexes involving such compounds such as carbon monoxide, amines, phosphines or olefins. The preferred palladium compounds are palladium (II) salts of organic acids including carboxylates with $C_{(2-6)}$ aliphatic acids. Palladium (II) acetate is particularly preferred. There also can be used in combination with palladium catalyst, tetraalkylammonium halide or tetraalkylphosphonium halide, such as the chlorides and bromides and particularly the bromides. Alkyl groups of the alkyl ammonium halides are primary and secondary alkyl groups containing about 1-8 carbon atoms. Tetra-n-butylammonium bromide is particularly preferred.

Aromatic organic amines which have been found effective as organic cocatalysts in the practice of the present invention as part of the transition metal catalyst are terpyridines, such as 2,2':6',2''-terpyridine, 2,2':6',2''-4-thiomethylterpyridine and 2,2':6',2''-4-terpyridine-N-oxide. In addition to terpyridine, phenanthroline also can be used, such as 1,10-phenanthroline, 2,4,7,8-tetramethyl-1,10-phenanthroline, 4,7-diphenyl-1,10-phenanthroline and 3,4,7,8-tetramethyl-1,10-phenanthroline.

Inorganic cocatalysts which can be used as part of the transition metal catalyst are, for example, manganese or cobalt cocatalysts. For example, there can be used cobalt or manganese compounds, such as divalent or trivalent compounds, for example, salts such as halides and carboxylates and complexes with amines, diketones and carbon monoxide have been found effective. Cobalt (II) acetate is particularly preferred. It has been found that optimum selectivity i.e., optimizing the formation of aromatic carbonate and minimizing the formation of aromatic salicylate is achieved using the cobalt (II) catalyst. Inorganic cocatalysts also include cobalt complexes have pentadentate ligands. Organic materials which can be used to form pentadentate ligands with cobalt (II) salts are preferably Schiff bases, such as di-(salicylal)-3,3'-diamino-N-methyldipropylamine. In addition to Schiff bases, there also can be used organic materials, such as aromatic amines, aliphatic amines, aromatic ethers, aromatic or aliphatic amine ethers.

A procedure for preparing such cobalt complexes containing a pentadentate Schiff base ligand is shown by R.S. Drago et al, J.Am. Chem. Soc. 1985, 107, 2903 and Drago et al, Coordination Chemistry Review 79 (1987) 321. It is preferred to preform the cobalt Schiff base complex prior to its use in the carbonylation reaction mixture.

Solid drying agents, such as molecular sieves, can be used to improve yields. In some instances, carbon dioxide also can be used as a dessicant as taught in copending application serial no. 07/503,404, filed 4/2/90 now abandoned, and referenced in continuation application serial number 724,292, filed 07/01/91, now U.S. Pat. No. 5,132,447.

In order that those skilled in the art will be better able to practice the present invention reference is made to the drawing. The drawing shows a schematic of a gas flow reactor system for preparing aromatic organic carbonate capable of delivering in a continuous manner at a flow rate about 50 ml to 1000 ml and preferably about 300 ml to 600 ml per min, a mixture of carbon monoxide and oxygen maintained at a substantially constant molar ratio and partial pressures. The symbol "V" means manual valve and the symbol "P" means pressure gage.

More particularly, there is shown at 10 a carbon monoxide gas inlet and at 11, an oxygen inlet. 12 is a manifold vent, and 13 is an optional inlet for a gas, such as carbon dioxide. The reaction mixture can be fed into a low pressure reservoir at 20, or a high pressure reservoir at 21 which can be operated at a higher pressure than the reactor for the duration of the run. At 22 there is shown a reservoir outlet and at 23 a reservoir inlet. The gas feed pressure can be adjusted to about 50 psi over the desired reactor pressure at a reducing pressure regulator at 30. The gas can be further purified in scrubber 31 and then fed into a mass flow controller at 32 to allow for the previously described flow rates. The reactor feed gas can be heated in an oil bath at 33 having appropriate conduit means prior to being introduced to the reactor at 40. The reactor pressure can be controlled through manipulation of a back pressure regulator at 41. The reactor gas effluent may be either sampled for further analysis at 42 or vented to the atmosphere at 50. The reactor liquid can be sampled at 43. 45 is a condenser. An additional vent at 44 can allow for further system control, but is typically closed during the gas flow reaction.

In the practice of one form of the invention, the palladium catalyst, co-catalyst package, and aromatic organic hydroxy compound are charged to the reactor. The reactor is sealed. Carbon monoxide and oxygen are introduced into an appropriate reservoir within proportions previously defined, until a suitable pressure such as 2800 psi is achieved.

Circulation of condenser water is initiated and the oil bath temperature can be raised to 100° C. Conduit between the oil bath and the reactor can be heated using heat tape to a suitable temperature such as 100° C. The mass flow bypass can be opened and an appropriate accumulator valve can be opened and the reducing pressure regulator can be used to adjust the pressure. The reactor pressure can be further adjusted by the back pressure regulator. The mass flow bypass can be closed and the flow can be adjusted using the mass flow controller. Agitation of the reaction ingredients can be initiated once the reactor temperature is raised sufficiently to minimize the presence of solids such as phenol. Upon reaching a desirable reactor temperature, such as 100° C., aliquots can be taken to monitor the reaction.

Upon completion of the reaction, the temperature of the reaction mixture can be reduced and the reactor pressure reduced to atmospheric to allow for the recovery of the 1:1 aromatic organic carbonate-aromatic organic hydroxy compound adduct hereinafter "DPC/phenol". Formation of the DPC/phenol adduct can be achieved by allowing the reaction mixture to cool from a temperature of 110° C. to 25° C. and preferably about 50° C. to about 30° C.

Recovery of the DPC/phenol adduct from the reaction mixture can be achieved by conventional means such as filtration, decantation, centrifugation, etc.

The aromatic organic carbonate, or "DPC" can be recovered from the DPC/phenol adduct by heating the adduct to phenol distillation temperatures in the range of 40° C. to 180° C. under reduced pressure such as 60–110 torr. Alternatively other techniques, such as solvent capitalization also can be used.

When free of surface contamination, the DPC/phenol adduct is a crystalline material having a mp in the range of 50° C. to 52° C. It consists of about 69.5% by weight of DPC and about 30.5 % by weight of aromatic hydroxy compound or "phenol".

In order that those skilled in the art will be better able to practice the present invention, the following examples are given by way of illustration and not by way of limitation. All parts are by weight unless otherwise indicated.

EXAMPLE 1

There was added to a flow reactor, as shown in the drawing, under ambient conditions 60.29 g (641 mmol) of phenol, 4.082 g (12.7 mmol) of tetrabutylammonium bromide, 0.243 g (0.3027 mmol) of "CoSMDPT", a cobalt complex containing a pentadentate Schiff base ligand, or cobalt based di-(salicylal)-3,3'-diamino-N-methyldipropylamine, 0.0362 g (0.155 mmol) of terpyridine, and 0.0650 g (0.2895 mmol) of palladium diacetate (477 ppm palladium). In addition 26.27 g of molecular sieves (4 Angstrom) which were activated overnight at 300° C. were mounted in a perforated Teflon resin basket above the liquid level of the reaction mixture as a dessicant. The reactor vessel was sealed. There was then fed into the reactor a mixture of 7.1% of oxygen in carbon monoxide. The mixture was introduced at the flow rate of 350 ml/min as measured with a bubbler. The pressure was set to 1650 psi.

The reactor was heated to 110° C. over a 15 minute period. Stirring was initiated at 540–550 rpm once the reactor temperature reached 40° C. Upon reaching a reactor temperature of 110° C., aliquots were taken periodically for GC analysis in order to quantify the amount of diphenyl carbonate produced. At 0.5 hr, the yield of diphenyl carbonate was 9.79 g (14.26%). At 1.0 hr, the yield of diphenyl carbonate was 16.2 g (23.6%). At 2.0 hr, the yield of diphenyl carbonate was 23.1 g (33.7%). After the two hour sample was taken, the reaction mixture was cooled at 60° C., and depressurized to atmospheric pressure.

The above procedure was substantially repeated and the reaction mixture from the initial run at a temperature of about 50° C. was added to the second run reaction mixture at about 50° C. at atmospheric pressure.

The combined reaction mixtures were then allowed to cool to 40° C. which resulted in the separation of a diphenyl carbonate:phenol adduct. The adduct was recovered from the reaction mixture by vacuum filtration resulting in the recovery of 58.5 g of the adduct representing a 74% yield. The DPC/phenol adduct was then heated to a temperature of 120° C. and a pressure of 80 torr to effect the distillation of phenol which resulted in the recovery of about 33.4 g of diphenyl carbonate.

EXAMPLE 2

The mother liquor of the reaction mixture of Example 1 was analyzed by HPLC showing 39.4% diphenyl carbonate, 37.5% phenol and 1.15% phenyl salicylate. There was added 20.99 g of phenol to 29.83 g of the mother liquor which contained 850 ppm of soluble palladium. The procedure of Example 1 was repeated with respect to reaction temperature, gas feed composition, stirring rate and gas flow rate. Upon reaching a reactor temperature of 110° C., aliquots were taken periodically for GC analysis in order to quantify the amount of diphenyl carbonate produced. At 0.0 hr, the yield of DPC was 11.7 g (21.6%); at 0.5 hr, the yield of DPC was 13.0 g (24.2%); at 1.0 hr, the yield of diphenyl carbonate was 10.5 g (38.1%); at 2.0 hr, the yield of diphenyl carbonate was 24.8 g (46.1%).

The procedure of Example 1 was repeated except that there was used as the palladium catalyst, a mixture of 0.0674 g of palladium diacetate, 0.0348 g terpyridine, 0.0562 g cobalt diacetate, 0=4.084 g tetrabutylammonium bromide and 59.49 g phenol. The mixture had 501 ppm palladium. There was obtained a 39% yield of diphenyl carbonate after 3.5 hours in accordance with the procedure of Example 1.

EXAMPLE 4

The procedure of Example 1 was repeated except that there was used as the palladium catalyst, a mixture of 0.0660 g of palladium diacetate, 0.1218 g CoSMDPT, 4.07 g tetrabutylammonium bromide and 60.99 g phenol. The mixture had 479 ppm palladium. There was obtained a 39% yield of diphenyl carbonate after 3.5 hours in accordance with the procedure of Example 1.

Although the above examples are directed to only a few of the very many variables which can be used in the practice of the method of the present invention, it should be understood that the present invention is directed to the use of a much broader variety of aromatic organic hydroxy compounds, palladium catalyst and inorganic and organic cocatalyst as set forth in the description preceding these examples.

What is claimed is:

1. A method for making an aromatic organic carbonate by carbonylating an aromatic organic hydroxy compound in the presence of a transition metal catalyst, where at the termination of the carbonylation reaction, an aromatic organic carbonate precursor is produced in the form of a 1:1 adduct of aromatic organic hydroxy compound and aromatic organic carbonate, and the transition metal catalyst is sufficiently stable under ambient conditions to allow its reuse as part of the reaction mixture mother liquor after recovery of the aromatic organic carbonate precursor from the resulting reaction mixture, which method comprises,
   (1) charging a reactor with aromatic organic hydroxy compound and an amount of a transition metal catalyst which is sufficient to catalyze the carbonylation of the aromatic organic hydroxy compound,
   (2) introducing a mixture of oxygen and carbon monoxide into the reactor and thereafter agitating and heating the resulting mixture to a temperature of about 60° C. to about 150° C., while maintaining the total reaction pressure and the partial pressures of carbon monoxide and oxygen in the mixture substantially constant until the aromatic organic hydroxy compound is substantially converted to aromatic organic carbonate,
   (3) allowing the resulting mixture of (2) to cool to a temperature of from about 50° C. to about 25° C., to form a 1:1 molar adduct of aromatic organic carbonate and aromatic organic hydroxy compound
   (4) recovering the 1:1 molar aromatic adduct from the reaction mixture of (3), and/or,
   (5) adding make-up aromatic organic hydroxy compound directly to the resulting reaction mixture mother liquor of (4), and,
   (6) recovering the aromatic organic carbonate from the 1:1 molar aromatic adduct of (4), where the transition metal catalyst is a member selected from the group consisting of,
   (a) a mixture consisting essentially of
      (i) 1 gram atom, per 800–10,000 moles of aromatic organic hydroxy compound, of a palladium material selected from catalytically active palladium or chemically combined palladium,
      (ii) 0.5–5.0 gram atom, per gram atom of palladium, of metal in the form of a cocatalyst selected from divalent or trivalent cobalt or manganese or copper compounds selected from the class consisting of salts, complexes with diketones, and complexes with carbon monoxide,
      (iii) 0.1 to 2 moles, per gram atom of palladium, of an aromatic organic amine selected from terpyridines, phenanthrolines and quinolines, and
      (iv) 10 to 100 moles, per gram atom of palladium, of a quaternary ammonium halide, and
   (b) a mixture consisting essentially of
      (v) 1 gram atom, per 800–10,000 moles of aromatic organic hydroxy compound of the palladium material of (a) (i),
      (vi) 0.5 to 5 gram atoms of cobalt, per gram atom of palladium, of a cobalt cocatalyst comprising a cobalt complex containing a pentadentate organic ligand, and a mixture of 0 to 0.5 moles of an aromatic amine of (a) (iii), per gram atom of cobalt of such cobalt complex containing a pentadentate ligand, and
      (vii) 10 to 100 moles, per gram atom of palladium, of a quaternary ammonium or phosphonium halide of (a) (iv).

2. A method in accordance with claim 1 where the aromatic organic carbonate precursor is an adduct of diphenyl carbonate and phenol.

3. A method in accordance with claim 1 where the palladium material is palladium diacetate.

4. A method in accordance with claim 1 where the aromatic organic amine is terpyridine.

5. A method in accordance with claim 1 where the cobalt cocatalyst is a cobalt complex of the Schiff base di-(salicylal)-3,3'-diamino-N-methyldipropylamine.

6. A method in accordance with claim 1 where the quaternary ammonium halide is tetra-n-butylammonium bromide.

7. A method for making aromatic organic carbonate in accordance with claim 1 which comprises adding make-up aromatic organic hydroxy compound to the mother liquor of the carbonylation reaction mixture of step (4), further carbonylating the resulting mixture to produce aromatic organic carbonate, allowing the mixture to cool to produce a 1:1 molar adduct of aromatic organic carbonate and aromatic organic hydroxy compound, recovering the 1:1 molar adduct and thereafter heating the 1:1 molar adduct under reduced pressure to effect the separation of aromatic organic hydroxy compound.

8. A method in accordance with claim 7, where the aromatic organic hydroxy compound is phenol.

* * * * *